United States Patent [19]

Jensen

[11] Patent Number: 4,533,354
[45] Date of Patent: Aug. 6, 1985

[54] MEDICAL DRAINAGE BAG AND NON-RETURN VALVE ASSEMBLY

[75] Inventor: Ole R. Jensen, Rivervale, N.J.

[73] Assignee: E. R. Squibb & Sons, Inc., Princeton, N.J.

[21] Appl. No.: 432,072

[22] Filed: Sep. 30, 1982

[51] Int. Cl.³ .............................................. A61M 1/00
[52] U.S. Cl. ........................................ 604/323; 383/44; 604/335
[58] Field of Search .................... 604/323–326, 604/335, 350, 410, 416, 87, 89; 128/760, 761, 767, DIG. 24; 383/21, 36, 44, 45, 57, 904, 38–40

[56] References Cited

U.S. PATENT DOCUMENTS

| | | | |
|---|---|---|---|
| 2,310,505 | 2/1943 | Blackburn et al. | 128/295 |
| 2,841,198 | 7/1958 | Kwake | 150/2.1 |
| 3,106,159 | 10/1963 | Abramson | 128/DIG. 24 |
| 3,295,145 | 1/1967 | Ericson | 604/350 |
| 3,297,152 | 1/1967 | Corella et al. | 383/44 |
| 3,306,296 | 2/1967 | Moss | 128/295 |
| 3,374,939 | 3/1968 | McMenimen | 229/53 |
| 3,405,714 | 10/1968 | Moss | 128/295 |
| 3,559,651 | 2/1971 | Moss | 128/295 |
| 3,618,606 | 11/1971 | Brown | 128/283 |
| 3,780,739 | 12/1973 | Frank | 128/283 |
| 3,961,529 | 6/1976 | Hanifl | 128/767 |
| 4,078,568 | 3/1978 | Etes et al. | 128/283 |
| 4,084,590 | 4/1978 | Caraway | 604/335 |
| 4,300,560 | 11/1981 | Steers et al. | 128/283 |
| 4,319,573 | 3/1982 | Whitlock | 640/323 |

FOREIGN PATENT DOCUMENTS

| | | | |
|---|---|---|---|
| 1066427 | 4/1967 | United Kingdom | 383/44 |
| 1139715 | 1/1969 | United Kingdom | . |
| 1343882 | 1/1974 | United Kingdom | . |
| 2048680 | 12/1980 | United Kingdom | . |

Primary Examiner—Stephen C. Pellegrino
Assistant Examiner—J. L. Kruter
Attorney, Agent, or Firm—Lerner, David, Littenberg, Krumholz & Mentlik

[57] ABSTRACT

A drainage bag employs a non-return valve assembly including at least one baffle positioned between the top and bottom of the bag. Each baffle extends completely across the interior of the bag and includes an upper portion which is continuously attached to one face of the bag and a lower portion which is attached to an opposite face of the bag at spaced intervals so as to form at least one opening adapted to permit liquid to flow readily from the top of the bag to the bottom of the bag while inhibiting liquid from flowing from the bottom of the bag to the top of the bag.

25 Claims, 7 Drawing Figures

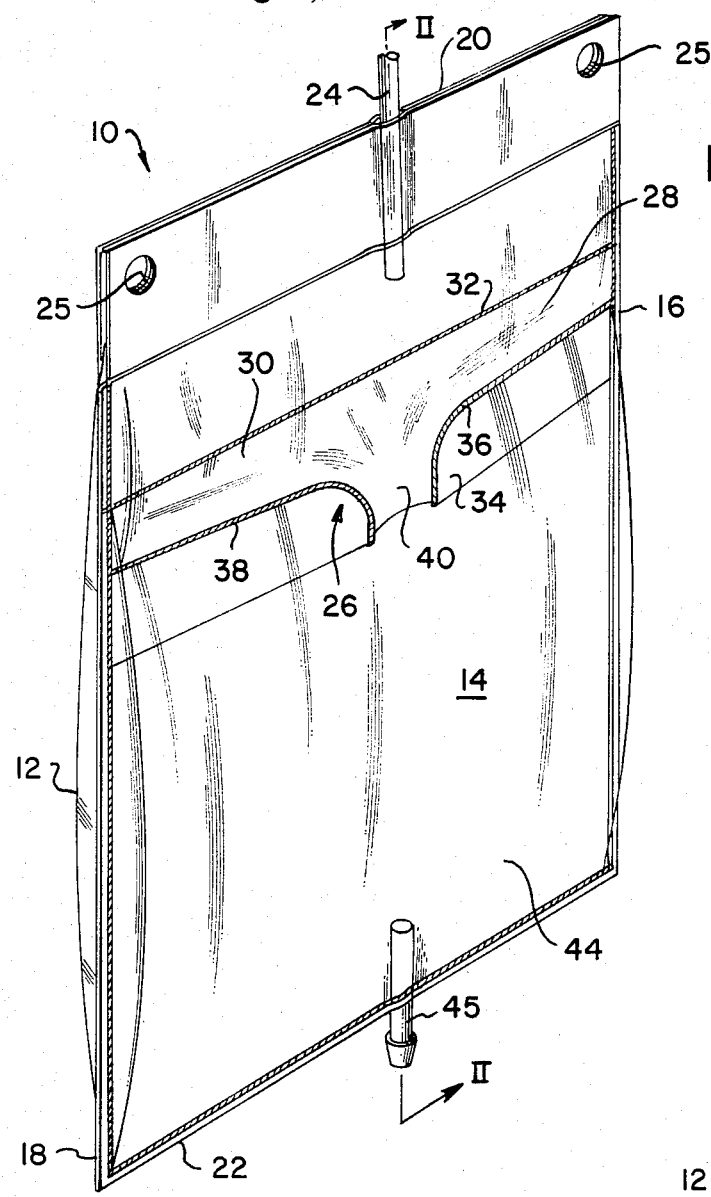
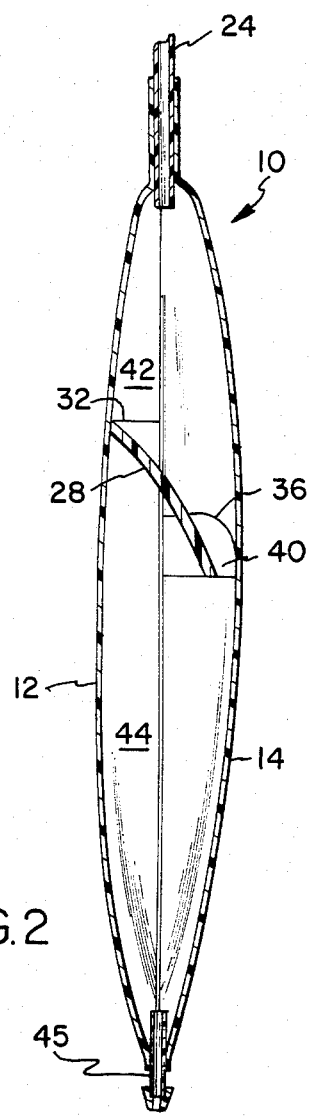
FIG. 1
FIG. 2

MEDICAL DRAINAGE BAG AND NON-RETURN VALVE ASSEMBLY

FIELD OF THE INVENTION

The present invention relates to drainage bags, and, more particularly, to such bags which are adapted to be applied to an individual for the purpose of collecting liquid, such as urine or some other type of liquid-like waste material, expelled from the individual's body. As used herein, the term "drainage bag" includes ileostomy bags, ureterostomy bags and the like, such as urinary and fistula bags.

BACKGROUND OF THE INVENTION

Drainage bags are commonly used for individuals who have undergone abdominal surgery involving a colostomy, ileostomy, ureterostomy or the like. Such surgical procedures necessitate the diversion of a bowel or urinary duct through a stoma formed in the individual's abdominal wall, whereby liquids and other waste materials may be discharged from the body through the stoma. The drainage bags are applied to the body of the individual so as to communicate with the stoma for receiving the liquids and waste materials expelled therefrom. Inasmuch as the discharges from the stoma are usually involuntary, the drainage bags are generally worn continuously, except when they are being replaced by another such bag.

Drainage bags are also useful for receiving urine from individuals who have ailments which impair their ability to control the release of urine. If the individuals are not bedridden, the bags are typically worn while the individual moves about from place to place.

All of the drainage bags described above suffer from a common problem. This problem involves the backflow of liquid in the bag as the individual moves about. Such backflow causes an unsanitary condition and, in addition, can cause the individual discomfort resulting from skin irritation and possibly infection.

In the past, there have been various attempts to overcome the backflow problem associated with drainage bags by providing the bags with one-way flap valves designed to permit liquid flow in one direction but not in an opposite direction. Such one-way valves are disclosed, for instance, in U.S. Pat. Nos. 4,084,590; 3,780,739 and 3,618,606. The flap valves disclosed in these patents and all of the other known flap valves for drainage bags require at least two plastic flaps to form the valves. Thus, the prior art flap valves can be rather expensive to manufacture because they require two layers of plastic. Also, the prior art valves are either attached to a catheter tube which extends into the bags between the sides thereof or to the sides of the bags themselves. As the bags with the valves attached to the sides thereof become filled with liquid, they assume a generally cylindrical shape, causing the two side seams of the bags to move closer to each other and, consequently, the flaps, which are normally flat, to become draped or folded. Such draping or folding of the flaps inhibits their proper closing, whereby fluid may pass through the valves in both directions rather than in just one direction.

SUMMARY OF THE INVENTION

The problems and disadvantages discussed above are overcome in accordance with the present invention by providing a unique drainage bag which incorporates a new and improved non-return valve assembly. More particularly, the valve assembly includes at least one baffle positioned intermediate the top and bottom of the bag and extending across the bag from its left side to its right side. Each baffle has an upper portion which is continuously attached to one face of the bag from the left side of the bag to the right side of the bag and a lower portion which is attached to an opposite face of the bag at spaced intervals between the left side of the bag and the right side of the bag. By this construction, at least one opening is formed along the bottom portion of the baffle, the opening or openings being positioned adjacent to the front or back face of the bag so as to permit liquid to flow readily from the top of the bag to the bottom of the bag while inhibiting liquid from flowing from the bottom of the bag to the top of the bag.

In one embodiment, each baffle is attached to the opposite face of the bag along a first curved path extending inwardly from the left side of the bag and a second curved path extending inwardly from the right side of the bag. The first and second curved paths, which are convex relative to the top of the bag, converge to form a single generally funnel-shaped opening therebetween.

In another embodiment, the lower portion of each baffle is attached to the opposite face of the bag along a plurality of inverted U-shaped paths. By this construction, a plurality of funnel-shaped openings is provided.

If a plurality of baffles is employed, an upper portion of one baffle can be attached to the front face of the bag, while a lower portion is attached to an adjacent surface of an underlying baffle rather than to the back face of the bag. By providing a sampling port in the front face of the bag between these two baffles, liquid samples may be removed from the bag by a syringe inserted through the port. When not in use, the sampling port is sealed from within the bag by the non-return valve formed as a result of attaching the baffles to each other.

BRIEF DESCRIPTION OF THE DRAWINGS

For a more complete understanding of the present invention, reference is made to the following detailed description of certain exemplary embodiments considered in conjunction with the accompanying drawings, in which:

FIG. 1 is a perspective view of one exemplary embodiment of a drainage bag constructed in accordance with the present invention;

FIG. 2 is a cross-sectional view, taken along line II—II of FIG. 1 and looking in the direction of the arrows, of the drainage bag shown in FIG. 1;

DETAILED DESCRIPTION OF THE EXEMPLARY EMBODIMENTS

While the present invention is applicable to any type of drainage bag, it is especially suitable for use in connection with urine bags. Thus, the present invention will be described with particular reference to a urine bag.

Figure 3:
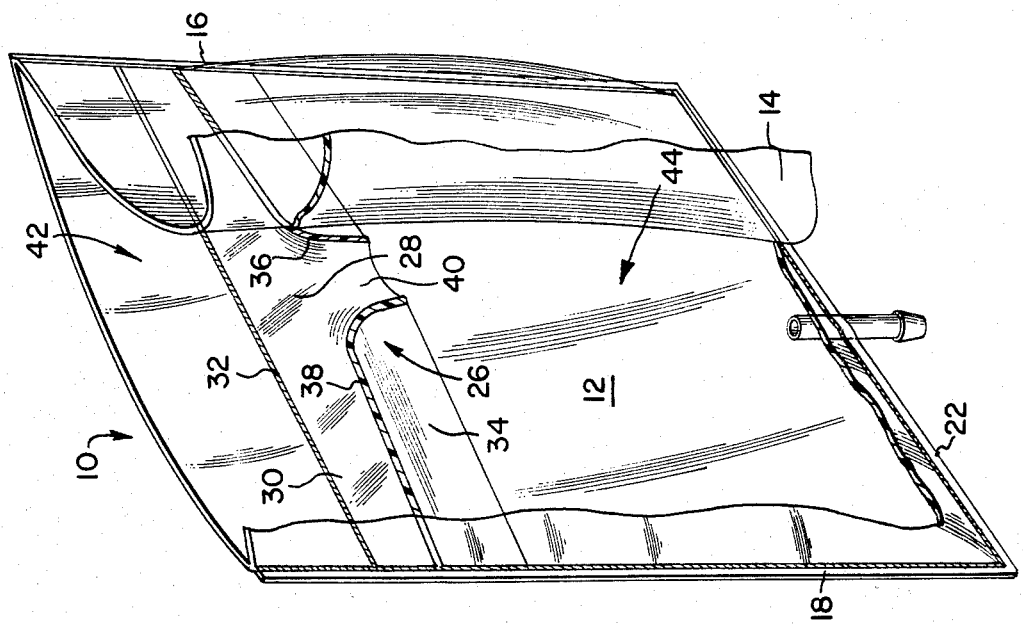
FIG. 3 is another perspective view of the drainage bag of FIG. 1, a portion of the drainage bag being broken away to facilitate consideration and discussion.

Referring to FIGS. 1-3, there is shown a urine bag 10 of the night or hospital type having a front face 12, a back face 14, a left side 16, a right side 18, a top 20 and a bottom 22. The top 20 of the urine bag 10 includes a catheter tube 24 adapted to deliver urine from an individual to the urine bag 10 and a pair of holes 25 adapted to hang the bag 10 from a suitable support structure. Typically, the urine bag 10 is made from two sheets of a flexible transparent material, such as polyvinlychloride, having a thickness in a range of from about 0.1 mm to about 0.2 mm. The sheets are heat sealed or R.F. welded together at their peripheries to form a liquid-tight enclosure.

A non-return valve 26 is positioned in the urine bag 10 between the top 20 and the bottom 22 thereof. The non-return valve 26 includes a baffle 28 which extends across the urine bag 10 from its left side 16 to its right side 18. The baffle 28, which is preferably made from the same flexible transparent material as the urine bag 10 itself, has an upper end 30 which is attached to the front face 12 of the urine bag 10 by a weld 32 extending continuously across the front face 12 of the urine bag 10 from its left side 16 to its right side 18. A lower end 34 of the baffle 28 is attached to the back face 14 of the urine bag 10 by two curved welds 36, 38. The weld 36 extends inwardly from the left side 16 of the urine bag 10, while the weld 38 extends inwardly from the right side 18 of the urine bag 10. The curved welds 36, 38, both of which are convex relative to the top 20 of the urine bag 10, converge to form a single generally funnel-shaped opening 40 therebetween. The opening 40 is sized to as to permit the free flow of urine from the catheter tube 24 in the top 20 of the urine bag 10 to the bottom 22 of the urine bag 10. Thus, the baffle 28 divides the urine bag 10 into an upper receiving compartment 42 and a lower storage compartment 44. A drain valve 45, which is located in the bottom 22 of the bag 10, communicates with the storage compartment 44 to permit the controlled drainage of collected urine therefrom.

In operation, the urine bag 10 is usually attached to a leg of an individual by a strap or some other suitable type of device. A tube or hose transports urine through the inlet 24 of the urine bag 10 and into the receiving compartment 42. From the receiving compartment 42, the urine flows into the storage compartment 44 through the opening 40 formed by the baffle 28. When the urine bag 10 is pressurized (e.g., if the urine bag 10 is squeezed while urine is present in the storage chamber 44), the pressure in the storage chamber 44 is greater than the pressure in the receiving chamber 42, thereby causing the baffle 28 to contact the back face 14 of the urine bag 10 and automatically close the opening 40. Thus, the baffle 28 inhibits the back flow of the urine from the storage compartment 44 to the receiving compartment 42. The baffle 28 also functions to limit the expansion of the urine bag 10 as a result of the urine stored in the storage compartment 44, whereby the urine bag 10 remains as inconspicuous as possible.

Three other exemplary embodiments of the present invention are illustrated in FIGS. 4—7. The various elements illustrated in FIGS. 4—7 which correspond to the elements described above with respect to the embodiment of FIGS. 1—3 have been designated by corresponding reference numerals increased by one hundred, two hundred and three hundred, respectively. Unless otherwise stated, the embodiments of FIGS. 4—7 operate in the same manner as the embodiment of FIGS. 1—3.

Figure 4:
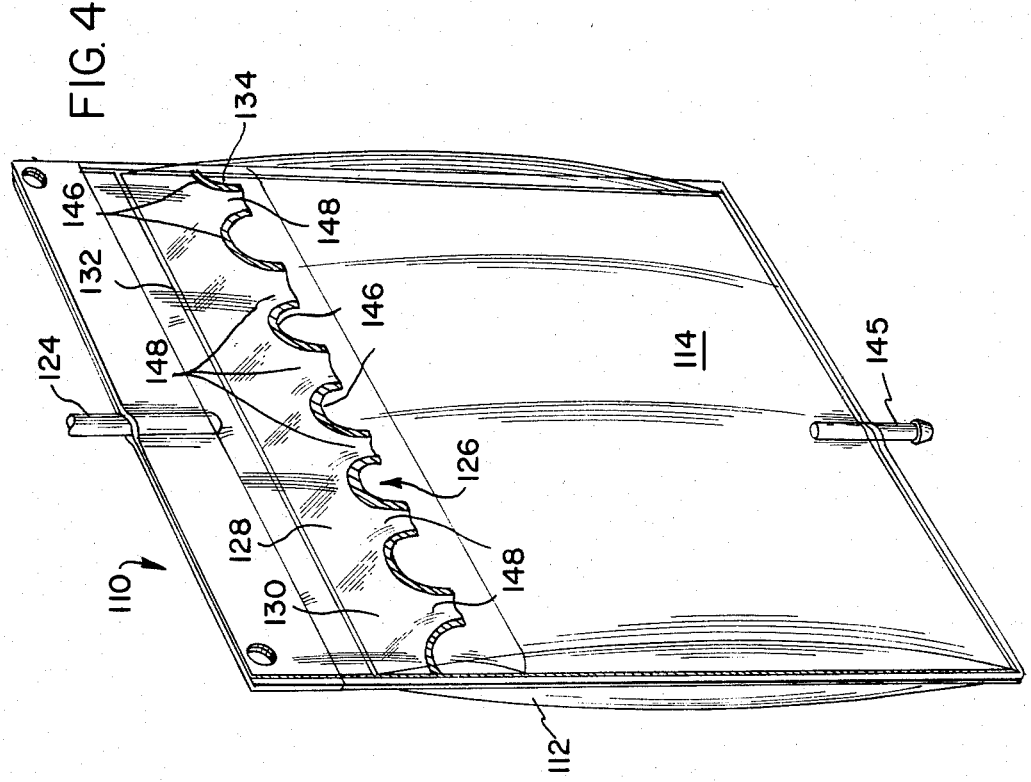
FIG. 4 is a perspective view of a second exemplary embodiment of a drainage bag constructed in accordance with the present invention.

Referring to FIG. 4, a urine bag 110 of the night or hospital type is provided with a non-return valve 126 which includes a baffle 128. An upper end 130 of a baffle 128 is attached to a front face 112 of the urine bag 110 by a continuous weld 132. The baffle 128 has a lower end 134 which is attached to a back face 114 of the urine bag 110 by inverted U-shaped welds 146 so as to form a plurality of openings 148.

Figure 5:
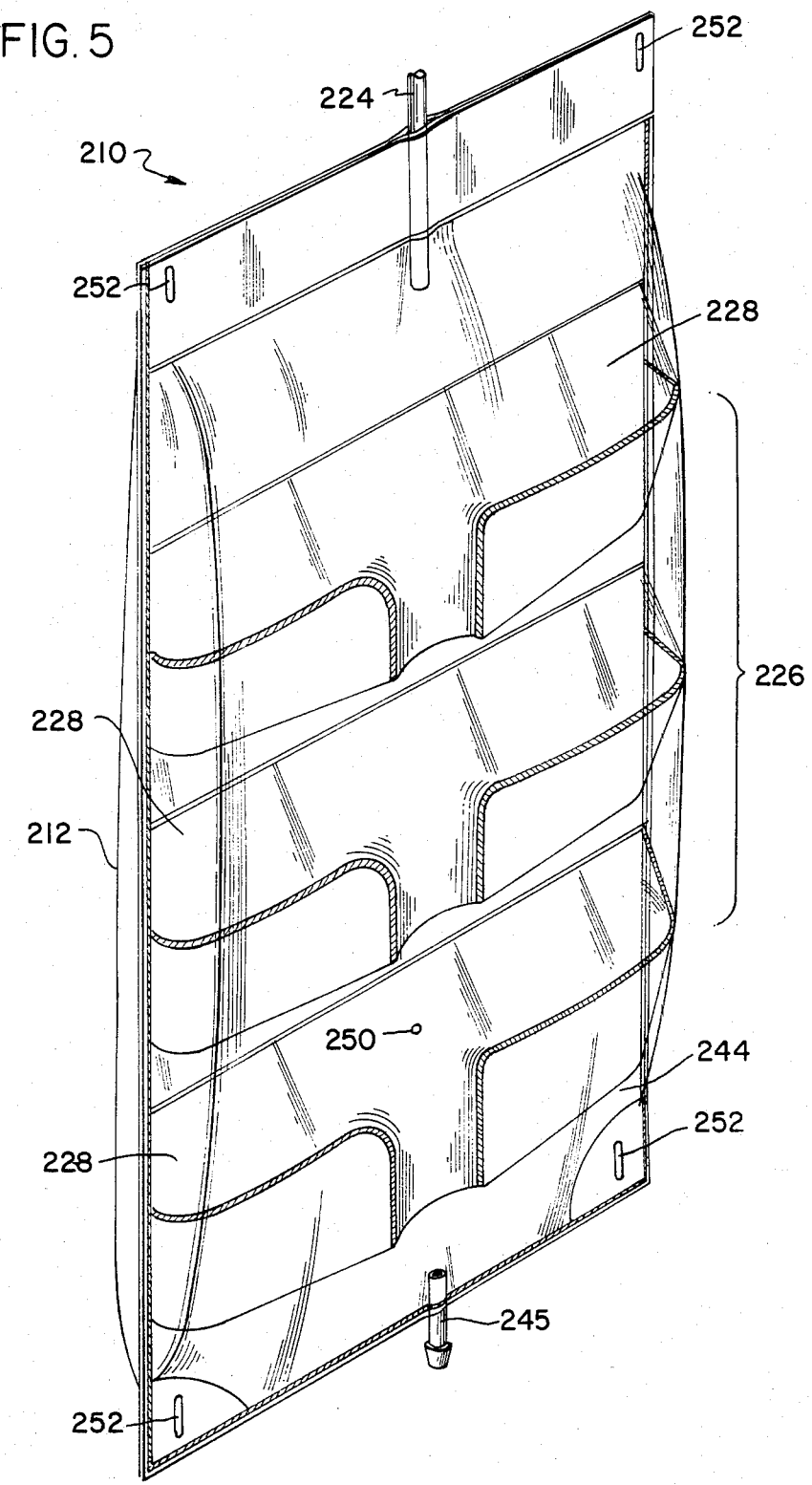
FIG. 5 is a perspective view of a third exemplary embodiment of a drainage bag constructed in accordance with the present invention.

In FIG. 5, there is shown a leg type urine bag 210 having a non-return valve assembly 226 which includes a plurality of baffles 228. In addition to inhibiting back flow of urine from a storage compartment 244 and limiting the amount of expansion of the urine bag 210 as a result of the urine stored in the storage compartment 244, the lowermost two of the baffles 228 perform an anti-sloshing function. A hole 250 may be provided in at least the lowermost one of the baffles 228, in order to permit the controlled back flow of urine in the event that the urine bag 210 is compressed or squeezed. Accordingly, the hole 250 functions as a pressure relief valve to avoid the possible rupturing of the urine bag 210 if the urine contained in the storage compartment 244 is overpressurized. In order to attach the bag 210 to a leg of an individual, the bag 210 is provided with slits 252, which are located and shaped so as to receive a pair of straps (not shown) adapted to strap the bag 210 to the individual's leg.

Figure 6:
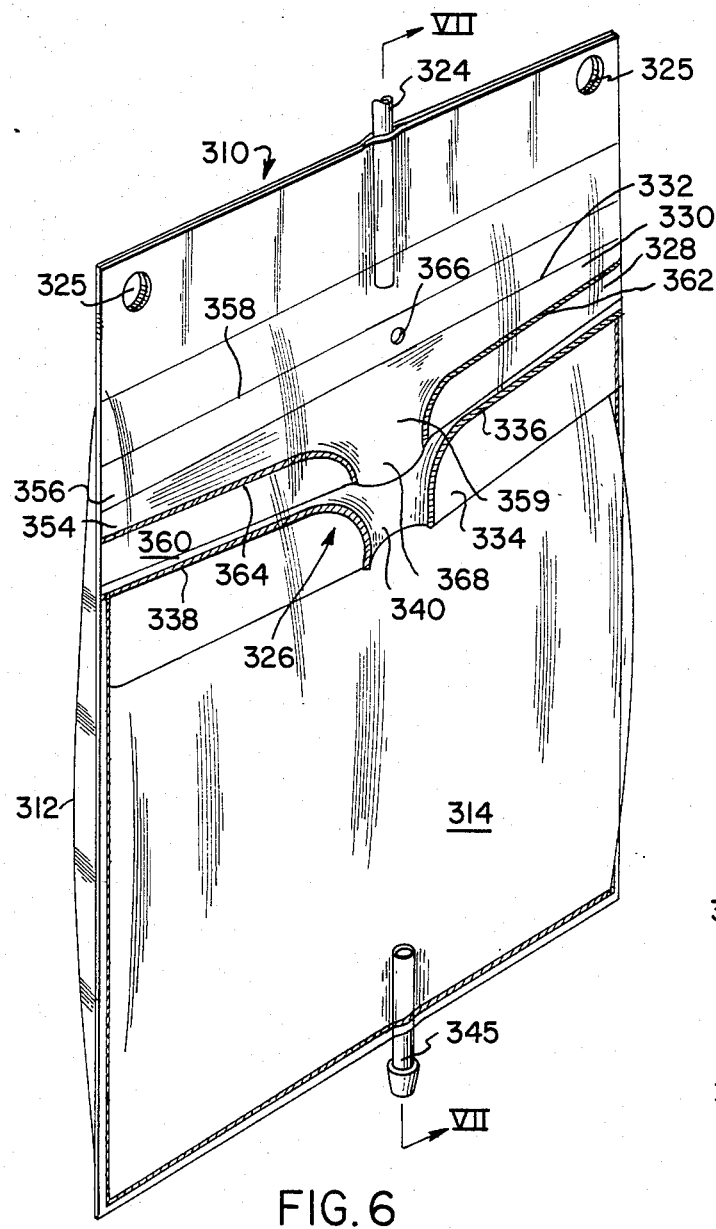
FIG. 6 is a perspective view of a fourth exemplary embodiment of a drainage bag constructed in accordance with the present invention.
Figure 7:
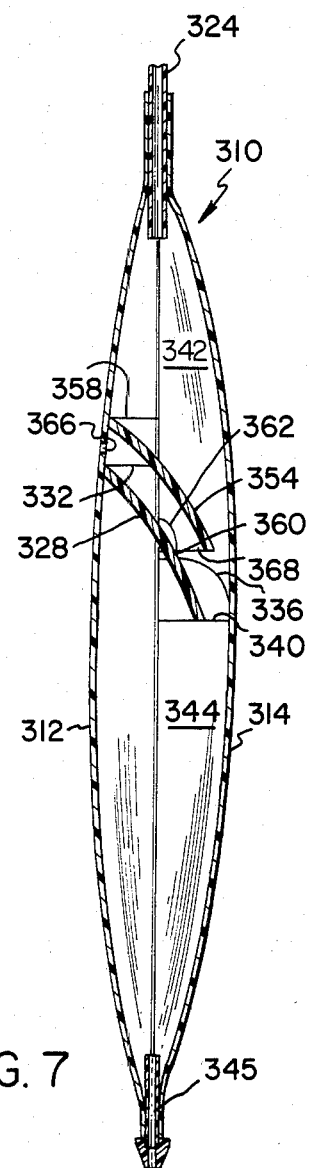
FIG. 7 is a cross-sectional view, taken along line VII—VII in FIG. 6 and looking in the direction of the arrows, of the drainage bag shown in FIG. 6.

With reference now to FIGS. 6 and 7, a urine bag 310 of the night or hospital type is equipped with a non-return valve assembly 326, which includes two baffles 328, 354. The baffle 328 has an upper end 330, which is attached to a front face 312 of the bag 310 by a continuous weld 332, and a lower end 334, which is attached to a back face 314 of the bag 310 by two curved welds 336, 338. An upper end 356 of the baffle 354 is attached to the front face 312 of the bag 310 by a continuous weld 358, while a lower end 359 of the baffle 354 is attached to an adjacent surface 360 of the baffle 328 by two curved welds 362, 364. An open port 366 is formed in the front face 312 of the bag 310 between the baffles 328, 354. The port 366 is dimensioned so as to receive a syringe. Thus, when an opening 340 formed between the back face 314 of the bag 310 and the baffle 328 is closed by, for instance, manually pinching the front face 312 against the back face 314, a syringe inserted through the port 366 can be used to withdraw a sample from liquid temporarily collected in a receiving chamber 342 immediately upon its discharge from a catheter tube 324. In normal use (i.e., when the opening 340 is open), the baffle 354, which functions in a manner similar to the baffle 328, permits the free flow of urine from the receiving chamber 342 to a storage chamber 344 through an opening 368, while preventing urine in the storage chamber 344 from being inadvertently or accidentally discharged from the bag 310 through the port 366.

It will be understood that the embodiments described herein are merely exemplary and that a person skilled in the art may make many variations and modifications without departing from the spirit and scope of the invention. For instance, the openings formed by the baffles can be positioned adjacent to the front faces of the urine bags, rather than the back faces. In a further modification, the urine bags may be adapted to receive liquid discharged from a stoma, rather than from a catheter tube. In such a modification, the catheter tubes would be replaced with a stoma aperture located in one face of the bags and communicating with the receiving chambers. An adhesive faceplate, such as the one illustrated in U.S. Pat. No. 4,084,590, or a mechanical means, such as the one shown in U.S. Pat. No. 4,300,560, would surround the stoma aperture to attach the bags to a patient. Also, besides polyvinlychloride, the urine bags can be made from other similar materials, such as polyethylene. All such modifications and variations are intended to be included within the scope of the invention as defined in the appended claims.

I claim:

1. A non-return valve assembly for a medical drainage bag adapted to collect body fluids which includes a front face, a back face, a left side, a right side, a bottom and a top, which top has an inlet provided therein, said non-return valve comprising at least one baffle positioned intermediate the top and bottom of the bag and extending across the bag from its left side to its right side, each baffle being formed by a single, unitary piece of flexible material having an upper portion continuously attached to one of the faces only along a seam positioned below the inlet provided in the top of the bag and extending from the left side of the bag to the right side of the bag and a lower portion attached directly to the other face at spaced intervals between the left side of the bag and the right side of the bag to thereby form at least one opening positioned adjacent to the other face of the bag so as to permit liquid to flow readily from the top of the bag to the bottom of the bag while inhibiting liquid from flowing from the bottom of the bag to the top of the bag.

2. A non-return valve assembly according to claim 1, wherein said lower portion of each baffle is attached to the other face of the bag along a first curved path extending inwardly from the left side of the bag and a second curved path extending inwardly from the right side of the bag, said first and second curved paths being convex relative to the top of the bag and converging to form a single generally funnel-shaped opening therebetween.

3. A non-return valve assembly according to claim 1, wherein said lower portion of each baffle is attached to the other face of the bag along a plurality of inverted U-shaped paths, whereby a plurality of openings is provided.

4. A non-return valve assembly according to claim 1, wherein there are a plurality of baffles arranged one above the other between the top and bottom of the bag.

5. A non-return valve assembly according to claim 4, wherein said upper portion of each baffle is attached to the front face of the bag and said lower portion of each baffle is attached to the back face of the bag.

6. A non-return valve assembly according to claim 4, wherein said upper portion of one baffle is attached to the front face of the bag and said lower portion of said one baffle is attached to an adjacent surface of another baffle located directly beneath said one baffle and not to the back face of the bag, whereby a liquid sample may be removed from between said baffles through an open port provided in the front face of the bag.

7. A non-return valve assembly according to claim 4, wherein said lower end of each baffle is attached to the back face of the bag along a first curved path extending inwardly from the left side of the bag and a second curved path extending inwardly from the right side of the bag, said first and second curved paths being convex relative to the top of the bag and converging to form a single generally funnel-shaped opening therebetween.

8. A non-return valve assembly according to claim 4, wherein said lower end of each baffle is attached to the back face of the bag along a plurality of inverted U-shaped paths, whereby a plurality of openings is provided.

9. A non-return valve assembly according to claim 1 or 4, wherein each baffle is made from a flexible transparent plastic.

10. A non-return valve assembly according to claim 9, wherein said flexible transparent plastic is selected from a group consisting of polyvinlychloride and polyethylene.

11. A medical drainage bag adapted to collect body fluids, comprising a front face, a back face, a left side, a right side, a top, having an inlet therein, a bottom and a non-return valve assembly which includes at least one baffle positioned intermediate the top and bottom of the bag and extending across the bag from its left side to its right side, each baffle being formed by a single, unitary piece of flexible material having an upper portion continuously attached to one of the faces only along a seam positioned below the inlet provided in the top of the bag and extending from the left side of the bag to the right side of the bag and a lower portion attached directly to the other face at spaced intervals between the left side of the bag and the right side of the bag to thereby form at least one opening positioned adjacent to the other face of the bag so as to permit liquid to flow readily from the top of the bag to the bottom of the bag while inhibiting liquid from flowing from the bottom of the bag to the top of the bag.

12. A drainage bag according to claim 11, wherein the lower portion of each baffle is attached to the other face of the bag along a first curved path extending inwardly from the left side of the bag and a second curved path extending inwardly from the right side of the bag, the first and second curved paths being convex relative to the top of the bag and converging to form a single generally funnel-shaped opening therebetween.

13. A drainage bag according to claim 11, wherein the lower portion of each baffle is attached to the other face of the bag along a plurality of inverted U-shaped paths, whereby a plurality of openings is provided.

14. A drainage bag according to claim 11, wherein said non-return valve assembly includes a plurality of baffles arranged one above the other between the top and bottom of the bag.

15. A drainage bag according to claim 14, wherein the upper portion of each baffle is attached to the front face of the bag and the lower portion of each baffle is attached to the back face of the bag.

16. A drainage bag according to claim 14, wherein the upper portion of a first baffle is attached to the front face of the bag and the lower portion of the first baffle is attached to an adjacent surface of a second baffle located directly beneath the first baffle and not to the back face of the bag, whereby a liquid sample may be removed from between the first and second baffles through an open port provided in the front face of the bag.

17. A drainage bag according to claim 14, wherein the lower end of each baffle is attached to the back face of the bag along a first curved path extending inwardly from the left side of the bag and a second curved path extending inwardly from the right side of the bag, said first and second curved paths being convex relative to the top of the bag and converging to form a single generally funnel-shaped opening therebetween.

18. A drainage bag according to claim 14, wherein the lower end of each baffle is attached to the back face of the bag along a plurality of inverted U-shaped paths, whereby a plurality of openings is provided.

19. A drainage bag according to claim 14, wherein at least a lowermost baffle includes a hole sized and shaped so as to permit the controlled back flow of liquid therethrough.

20. A drainage bag according to claim 11 or 14, wherein the bag and each baffle thereof are made from a flexible transparent plastic.

21. A drainage bag according to claim 20, wherein the flexible transparent plastic is selected from a group consisting of polyvinylchloride and polyethylene.

22. A non-return valve assembly for a medical drainage bag adapted to collect body fluids which includes a front face, a back face, a left side, a right side, a top and a bottom, said non-return valve comprising a plurality of baffles arranged one above the other between the top and bottom of the bag and extending across the bag from its left side to its right side, each baffle being formed by a single, unitary piece of flexible material having an upper portion continuously attached to the front face only from the left side of the bag to the right side of the bag and a lower portion attached directly to the back face at spaced intervals between the left side of the bag and the right side of the bag to thereby form at least one opening positioned adjacent to the back face of the bag so as to permit liquid to flow readily from the top of the bag to the bottom of the bag while inhibiting liquid from flowing from the bottom of the bag to the top of the bag.

23. A non-return valve assembly for a medical drainage bag adapted to collect body fluids which includes a front face, a back face, a left side, a right side, a top and a bottom, said non-return valve comprising a first baffle positioned intermediate the top and bottom of the bag and extending across the bag from its left side to its right side, said first baffle being formed by a single, unitary piece of flexible material having an upper portion continuously attached to the front face only from the left side of the bag to the right side of the bag and a lower portion attached directly to the back face at spaced intervals between the left side of the bag and the right side of the bag to thereby form at least one opening positioned adjacent to the back face of the bag so as to permit liquid to flow readily from the top of the bag to the bottom of the bag while inhibiting liquid from flowing from the bottom of the bag to the top of the bag, and a second baffle positioned intermediate the top and bottom of the bag directly above said first baffle and extending across the bag from its left side to its right side, said second baffle being formed by a single, unitary piece of flexible material having an upper portion continuously attached to the front face only from the left side of the bag to the right side of the bag and a lower portion attached directly to an adjacent surface of said first baffle, whereby a liquid sample may be removed from between said first and second baffles through an open port provided in the front face of the bag.

24. A medical drainage bag adapted to collect body fluids, comprising a front face, a back face, a left side, a right side, a top, a bottom and a non-return valve assembly which includes a plurality of baffles arranged one above the other between the top and bottom of the bag and extending across the bag from its left side to its right side, each baffle being formed by a single, unitary piece of flexible material having an upper portion continuously attached to the front face only from the left side of the bag to the right side of the bag and a lower portion attached directly to the back face at spaced intervals between the left side of the bag and the right side of the bag to thereby form at least one opening positioned adjacent to the back face of the bag so as to permit liquid to flow readily from the top of the bag to the bottom of the bag while inhibiting liquid from flowing from the bottom of the bag to the top of the bag.

25. A medical drainage bag adapted to collect body fluids, comprising a front face, a back face, a left side, a right side, a top and bottom and a non-return valve assembly which includes a first baffle positioned intermediate the top and bottom of the bag and extending across the bag from its left side to its right side, said first baffle being formed by a single, unitary piece of flexible material having an upper portion continuously attached to the front face only from the left side of the bag to the right side of the bag and a lower portion attached directly to the back face at spaced intervals between the left side of the bag and the right side of the bag to thereby form at least one opening positioned adjacent to the back face of the bag so as to permit liquid to flow readily from the top of the bag to the bottom of the bag while inhibiting liquid from flowing from the bottom of the bag to the top of the bag, and a second baffle positioned intermediate the top and bottom of the bag directly above said first baffle and extending across the bag from its left side to its right side, said second baffle being formed by a single, unitary piece of flexible material having an upper portion continuously attached to the front face only from the left side of the bag to the right side of the bag and a lower portion attached directly to an adjacent surface of said first baffle, whereby a liquid sample may be removed from between said first and second baffles through an open port provided in the front face of the bag.

* * * * *